(12) United States Patent
Heuscher (10) Patent No.: US 7,324,623 B2
(45) Date of Patent: Jan. 29, 2008

(54) COMPUTED TOMOGRAPHY SCANNER WITH LARGE GANTRY BORE

(75) Inventor: Dominic J. Heuscher, Aurora, OH (US)

(73) Assignee: Koninklijke Philips Electronics N. V., Eindhoven (NL)

( * ) Notice: Subject to any disclaimer, the term of this patent is extended or adjusted under 35 U.S.C. 154(b) by 0 days.

(21) Appl. No.: 10/564,715

(22) PCT Filed: Jul. 12, 2004

(86) PCT No.: PCT/IB2004/002271

§ 371 (c)(1),
(2), (4) Date: Jan. 13, 2006

(87) PCT Pub. No.: WO2005/004722

PCT Pub. Date: Jan. 20, 2005

(65) Prior Publication Data

US 2006/0159220 A1    Jul. 20, 2006

Related U.S. Application Data (60) Provisional application No. 60/487,389, filed on Jul. 15, 2003.

(51) Int. Cl.
*A61B 6/03*    (2006.01)
(52) U.S. Cl. .................... 378/9; 378/16; 378/19
(58) Field of Classification Search .............. 378/4, 378/9, 19, 16; 382/131
See application file for complete search history.

(56) References Cited

U.S. PATENT DOCUMENTS

| | | | | |
|---|---|---|---|---|
| 4,636,952 A | * | 1/1987 | Crawford | 378/14 |
| 4,991,190 A | * | 2/1991 | Mori | 378/9 |
| 5,068,882 A | | 11/1991 | Eberhard | 378/4 |
| 5,513,236 A | | 4/1996 | Hui | 378/15 |
| 5,724,400 A | * | 3/1998 | Swerdloff et al. | 378/65 |

(Continued)

FOREIGN PATENT DOCUMENTS

EP    1 005 257 A2    5/2000

(Continued)

OTHER PUBLICATIONS

Kachelreiss, et al., "ECG-correlated Image Reconstruction From Sub Second Multi-Slice Spiral CT Scans of the Heart", Med. Phys. 27(8), Aug. 2000 p. 1881-1902.

(Continued)

*Primary Examiner*—Chih-Cheng G Kao (57) ABSTRACT

A computed tomography scanner includes a rotating gantry (20) defining an examination region (16). A first radiation source (22) is disposed on the rotating gantry (20) and emits first radiation (32) into the examination region (16). A second radiation source (24) is disposed on the rotating gantry (20) and emits second radiation (36) into the examination region (16). The second radiation source (24) is angularly spaced around the gantry from the first radiation source (22). A first radiation detector (30, 30') receives the first radiation (32). A center of the first radiation detector (30, 30') is angularly spaced around the gantry from the first radiation source (22) by less than 180°. A second radiation detector (34) receives the second radiation (36). A center of the second radiation detector (34) is angularly spaced around the gantry from the second radiation source (24) by less than 180°.

26 Claims, 6 Drawing Sheets

U.S. PATENT DOCUMENTS

| | | |
|---|---|---|
| 5,848,117 A | 12/1998 | Urchuk et al. ............... 378/19 |
| 6,104,775 A | 8/2000 | Tuy ............................... 378/4 |
| 6,104,780 A * | 8/2000 | Hanover et al. ............. 378/92 |
| 6,154,516 A | 11/2000 | Heuscher et al. ............ 378/15 |
| 6,760,399 B2 * | 7/2004 | Malamud ....................... 378/9 |
| 6,895,077 B2 * | 5/2005 | Karellas et al. ............ 378/98.3 |
| 7,085,343 B2 * | 8/2006 | Shinno et al. ................ 378/9 |
| 2001/0011701 A1 * | 8/2001 | Such et al. ................ 250/250 |
| 2003/0108146 A1 | 6/2003 | Malamud .................... 378/19 |
| 2003/0128801 A1 * | 7/2003 | Eisenberg et al. ............ 378/19 |

FOREIGN PATENT DOCUMENTS

| | | |
|---|---|---|
| JP | 60073442 | 4/1985 |
| WO | WO 02/26134 A1 | 4/2002 |
| WO | WO 02/30282 A2 | 4/2002 |

OTHER PUBLICATIONS

Taguchi, et al., "High Temporal Resolution For Multislice Helical Computed Tomography", Med. Phys. 27 (2000) pp. 861-872.

* cited by examiner

COMPUTED TOMOGRAPHY SCANNER WITH LARGE GANTRY BORE

CROSS REFERENCE TO RELATED APPLICATIONS

This application claims the benefit of U.S. provisional application Ser. No. 60/487,389 filed Jul. 15, 2003, which is incorporated herein by reference.

The following relates to the diagnostic imaging arts. It finds particular application in interventional computed tomography, that is, in computed tomography imaging for providing visualization in interventional procedures, and will be described with particular reference thereto. However, it also finds application in other areas of computed tomography imaging that benefit from rapid imaging of a large field of view.

Computed tomography imaging is increasingly used to assist in interventional medical procedures. For example, biopsy of internal tissue benefits from using computed tomography imaging to determine and guide the needle route during the tissue extraction process. Computed tomography can also be used to monitor fluid drainage procedures. Complex oncology radiation therapy procedures are suitably preprogrammed using imaging and radiation absorption profiling data acquired by computed tomography imaging.

An interventional computed tomography scanner preferably has a large gantry bore to accommodate both the patient and instruments used in the interventional procedure. A large bore is also useful to accommodate patients who may be arranged in other than a prone position during the interventional procedure. The patient is positioned in the bore, with the organ or region that is the subject of the interventional procedure positioned at or near bore center. This central region of the field of view is of primary interest during the interventional procedure, and is preferably imaged at high spatial and temporal resolution.

Additionally, for many interventional procedures it is beneficial to provide imaging over a larger field of view surrounding the central region of primary interest. For instance, during a biopsy it is useful to image the needle throughout the needle route, preferably beginning with its initial insertion into the patient. Similarly, in radiation therapy the central region preferably contains the organ that is to receive therapy; however, the entire path of the radiation beam through the patient is preferably imaged to ascertain that there are no beam obstructions or sensitive critical structures that should be avoided.

Although it is beneficial to image both the central region containing the target organ and also surrounding regions, the imaging in the surrounding regions may be less critical and can be acquired at lower spatial and temporal resolution. Moreover, even though today's scanners typically contain an arc of uniform-size detectors, spatial resolution degrades as a function of the distance from scan center due to the focal spot optics. In spite of these optical limitations, existing computed tomography scanners attempt to provide a uniform spatial and temporal resolution throughout the field of view.

Existing computed tomography scanners generate a fan or conebeam of x-rays that interact with a generally circular or cylindrical imaging volume. The field of view is determined by the fan angle of the fan or conebeam, and the imaging volume is divided into voxels of a selected spatial size, based on detector geometry, and temporal resolution. As a result, if the x-ray beam is made large enough to interact with both the organ of interest and surrounding tissues, both the organ of interest and the surrounding tissues are images at the same spatial and temporal resolution. However, it is known that the image quality typically degrades for outlying portions of the imaging volume for various reasons, such as focus imperfections, increased x-ray scatter, reconstruction-related artifacts, and the like.

Thus, existing scanners acquire unnecessarily large quantities of data in the outlying areas of the imaging volume, and additionally these large quantities of data do not translate into correspondingly high quality reconstructed images of the outlying areas. Large imaging volume is obtained with these existing scanners at the expense of large and expensive x-ray tubes, large-area and correspondingly expensive high resolution x-ray detector arrays, and high data acquisition rates that translate into degraded image reconstruction performance.

In addition to a large bore and large field of view, an interventional computed tomography scanner preferably also has high temporal and spatial resolution. Temporal resolution is limited in part by the gantry rotation rate. A 180° segment of projection data, which is generally sufficient to perform image reconstruction, is acquired over about a half-rotation of the gantry. At a gantry rotation rate of 200 rpm, this corresponds to a temporal resolution of about 150 milliseconds.

Temporal and spatial resolution can be improved by addition of a second radiation source angularly offset from the first radiation source on the rotating gantry. By combining projection data of both radiation sources, temporal resolution is improved to about 75 milliseconds for the exemplary 200 rpm rotation rate. However, gantry space problems arise in attempting to integrate a second radiation source along with its power supply, cooling circuit, and other associated hardware onto the gantry of an interventional computed tomography scanner or other large bore, large field-of-view scanner. When each element of the radiation detectors is limited to receiving radiation from one of the two radiation sources, the angular displacement between the x-ray sources limits the fan angles. Limiting the fan angle disadvantageously limits the field of view.

The present invention contemplates an improved apparatus and method that overcomes the aforementioned limitations and others.

According to one aspect, a computed tomography imaging system is disclosed. A rotating gantry defines an examination region. A first radiation source is disposed on the rotating gantry and is arranged to emit first radiation into the examination region. A second radiation source is disposed on the rotating gantry and is arranged to emit second radiation into the examination region. The second radiation source is angularly spaced around the gantry from the first radiation source. A first radiation detector is arranged to receive the first radiation. A center of the first radiation detector is angularly spaced around the gantry from the first radiation source by less than 180°. A second radiation detector is arranged to receive the second radiation. A center of the second radiation detector is angularly spaced around the gantry from the second radiation source by less than 180°. A reconstruction processor reconstructs projection data acquired during gantry rotation by the first and second radiation detectors into one or more image representations.

According to another aspect, a computed tomography imaging system is disclosed. A rotating gantry defines an examination region. The examination region includes a central region that contains a center of rotation of the rotating gantry and a surrounding region that surrounds the central region. The rotating gantry further defines a gantry plane of gantry rotation and an axial direction. A first radiation source is disposed on the rotating gantry. The first radiation source produces first radiation directed into the examination region. A first radiation detector array is arranged to receive the first radiation after the first radiation passes through the examination region. The first detector array includes: a high resolution portion with detector elements of a first size that receive first radiation that passes through the central region; and a low resolution portion with detector elements of a second size that receive first radiation that passes through the surrounding region but not the central region. The second size is larger than the first size. A reconstruction processor reconstructs projection data acquired during gantry rotation by at least the first radiation detector array into an image representation.

According to yet another aspect, a computed tomography imaging method is provided. First radiation is passed through an examination region. The examination region includes a central region and a surrounding region. Central projections are measured corresponding to rays of first radiation that intersect the central region. The measuring uses a first high-resolution detector array that has a first spacing of detector elements. Surrounding projections are measured corresponding to rays of first radiation that intersect the surrounding region without intersecting the central region. The measuring uses a first low-resolution detector array that has a second spacing of detector elements which is larger than the first spacing. The central projections and the surrounding projections are reconstructed to generate a reconstructed image representation.

According to still yet another aspect, a computed tomography imaging method is provided. First and second angularly rotating and angularly offset asymmetric radiation beams are passed through an examination region. The first and second angularly rotating and angularly offset asymmetric radiation beams define a central region that is continuously sampled by both first and second asymmetric radiation beams during the angular rotating and a surrounding region that is not sampled over a portion of the angular rotating. The first and second asymmetric radiation beams are detected after said beams pass through the examination region to generate first and second radiation projection data. Voxels are reconstructed based on the first and second radiation projection data. The reconstructing includes smoothing projection data of voxels in a transition region between the central region and the surrounding region.

One advantage resides in improved temporal and spatial resolution for large bore, large field-of-view computed tomography scanners such as interventional computed tomography scanners.

Another advantage resides in providing high resolution in a central region of the examination region, coupled with a reduced resolution in a surrounding region of the examination region that surrounds the central region.

Another advantage resides in more efficient image reconstruction by reducing the amount of projection data acquired for the surrounding region which is of less interest, as compared with the central region that contains the principal subject of imaging.

Yet another advantage resides in providing simultaneous acquisition of dual energy projection data to provide enhanced contrast in reconstructed images.

Still yet another advantage resides in providing both angularly and axially offset radiation sources to improve spatial and/or temporal resolution.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
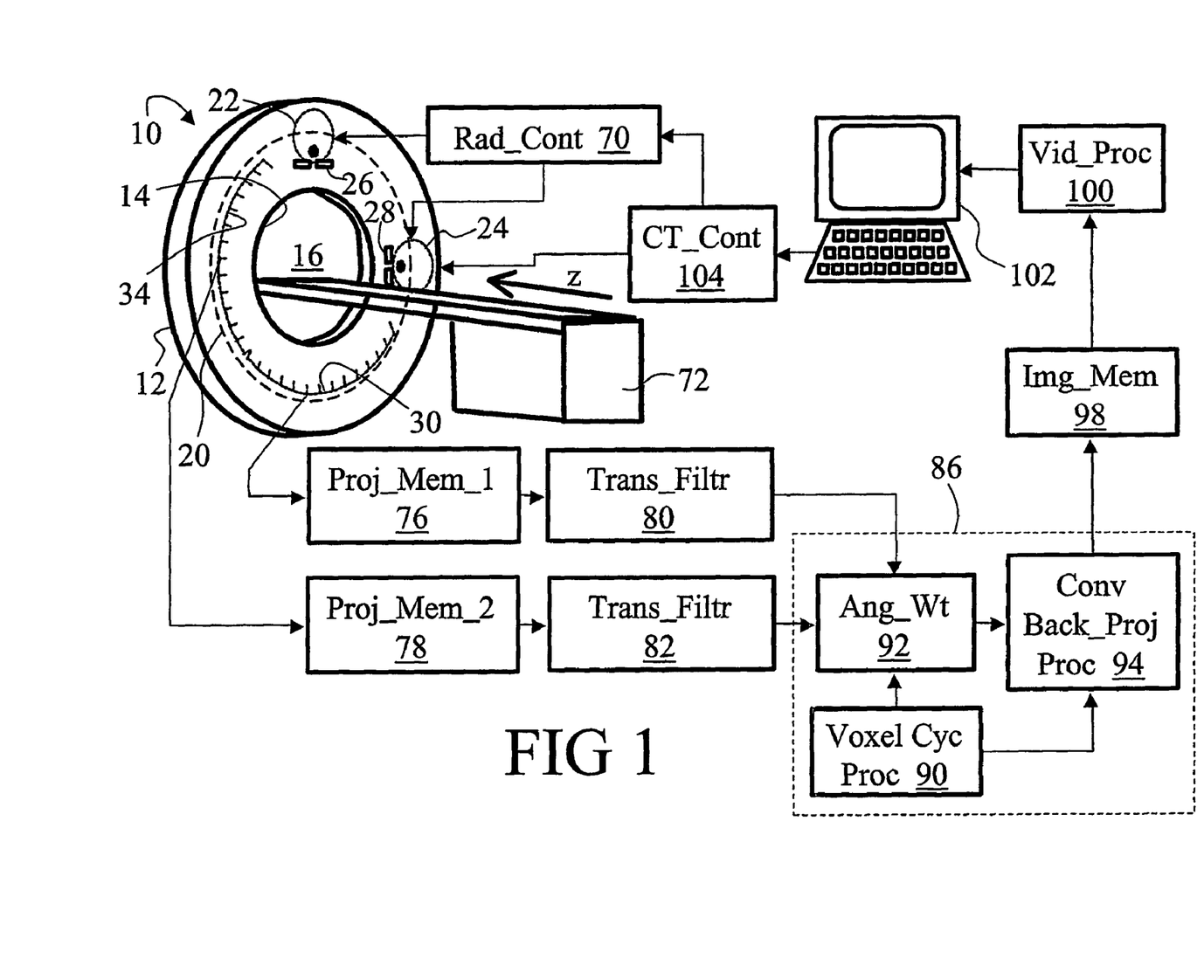
FIG. 1 diagrammatically shows an interventional computed tomography imaging system including two angularly spaced-apart radiation sources.
Figure 2:
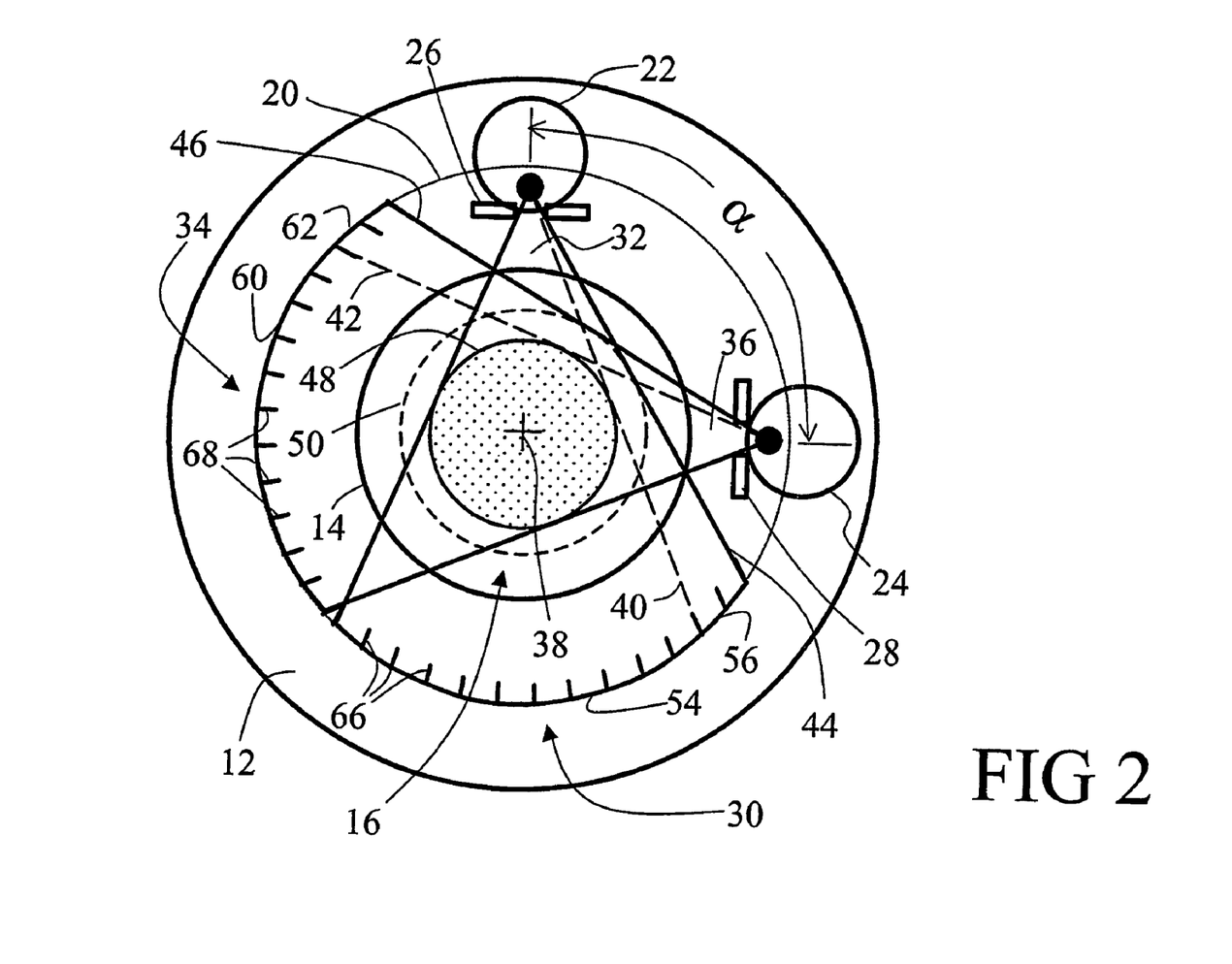
FIG. 2 diagrammatically shows the gantry of the computed tomography scanner of FIG. 1, with the radiation fans produced by the two radiation sources and the central and surrounding imaging regions shown.

With reference to FIGS. 1 and 2, a computed tomography imaging scanner 10 includes a stationary gantry 12 with a bore 14 that defines an examination region 16. For interventional applications, the bore 14 is preferably a large bore, such as a bore of around 800 mm diameter. However, the bore 14 can be smaller than this. A rotating gantry 20 (indicated diagrammatically in FIGS. 1 and 2) is rotatably mounted in the stationary gantry 12. First and second radiation sources 22, 24, which are preferably x-ray tubes collimated by collimators 26, 28 into fan or conebeams, are arranged on the rotating gantry 20 at an angular spacing of α around the gantry, where α preferably equals 90°. The radiation sources 22, 24 rotate with the rotating gantry 20.

A first radiation detector 30 is arranged to receive first radiation 32 produced by the first radiation source 22 after the first radiation 32 passes through the examination region 16. The first radiation detector 30 is arranged asymmetrically with respect to the first radiation source 22. That is, a center of the first radiation detector 30 is angularly spaced from the first radiation source 22 by less than 180° around the gantry. The first radiation detector 30 spans an angular interval of the gantry that, in the illustrated embodiment, is greater than 90° so as to enable imaging over a large field of view.

Similarly, a second radiation detector 34 is arranged to receive second radiation 36 produced by the second radiation source 24 after the second radiation 36 passes through the examination region 16. The second radiation detector 34 is arranged asymmetrically with respect to the second radiation source 24. That is, a center of the second radiation detector 34 is angularly spaced from the second radiation source 24 by less than 180° around the gantry. The second radiation detector 34 preferably spans an angular interval of the gantry that, in the illustrated embodiment, is greater than 90° so as to enable imaging over a large field of view.

With particular reference to FIG. 2, the asymmetric gantry geometry is described in more detail. A rotational center 38, that is, the center of gantry rotation, is indicated by crosshairs in FIG. 2. The first radiation source 22 is collimated by the collimator 26 to produce first radiation 32 in an expanding fan-beam or conebeam configuration such that the first radiation 32 expands at a fan-angle to substantially span the first radiation detector 30. Because the center of the first radiation detector 30 is spaced less than 180° from the first radiation source 22, the fan of the first radiation 32 is asymmetric, that is, off-center with respect to the rotational center 38. Similarly, the second radiation source 24 produces second radiation 36 in an expanding fan-beam or conebeam configuration that expands at a fan-angle to substantially span the second radiation detector 34. Because the center of the second radiation detector 34 is spaced less than 180° from the second radiation source 22, the fan of the second radiation 36 is also asymmetric or off-center with respect to the rotational center 38.

In a preferred embodiment, the asymmetry of the first and second radiation 32, 36 is adjustable. In this embodiment, the first radiation collimator 26 has a fixed edge defining a fixed first edge of the first radiation 32, and an adjustable edge that defines the amount of asymmetry. At a minimum setting of the collimator 26, a symmetric edge 40 (shown as a dashed line) of the first radiation 32 is selected. At this setting the first radiation 32 is generally symmetric. Similarly, the second radiation collimator 28 has a fixed edge, and an adjustable edge that at its minimum setting defines a symmetric edge 42. On the other hand, at a maximum setting of the collimator 26, a maximum asymmetric edge 44 of the first radiation 32 is selected. This provides maximum asymmetry of the first radiation 32. Similarly, at a maximum setting of the collimator 28, a maximum asymmetric edge 46 of the second radiation 36 is selected, providing maximum asymmetry of the second radiation 36.

Typically, the minimum settings of the collimators 26, 28 are used to reduce radiation exposure of the imaging subject when a large field of view is not particularly useful. Collimator settings that are intermediate between the minimum symmetric and maximum asymmetric settings can be employed to trade off between radiation exposure dosage and field of view. Although asymmetrically adjustable collimators 26, 28 advantageously enable control of radiation exposure of the subject, it is also contemplated to employ non-adjustable collimators that provide non-adjustable asymmetric radiation beams.

The asymmetric fan-beam or conebeam of the first and second radiation 32, 36 is suitably considered as a combination of symmetric and asymmetric beam components. The symmetric edge 40 separates the symmetric and asymmetric beam components of the first radiation 32, and the symmetric edge 42 separates the symmetric and asymmetric beam components of the second radiation 36. The symmetric beam components pass through and are centered on the rotational center 38. With the collimators 26, 28 at their minimum settings, only the symmetric beam component is operative. As the adjustable collimators 26, 28 are opened beyond their minimum settings, additional asymmetric beam portions are introduced. The asymmetric edges 44, 46 correspond to maximum asymmetric beam portions. Except where otherwise noted, hereinafter the collimators 26, 28 will be assumed to be at their maximum asymmetric settings to provide maximum asymmetry of the first and second radiation 32, 36, and maximum field of view.

During rotation of the rotating gantry 20 about the rotational center 38, the symmetric beam component of each of the first and second radiation fans or cones 32, 36 continuously irradiates a central region 48 of the examination region 16. The central region 48 contains and is centered on the rotational center 38. For any angular position of the gantry 20, the symmetric beam component of each of the two radiation fans 32, 36 irradiates every voxel contained in the central region 48. Since voxels contained in the central region 48 are continuously irradiated by both radiation sources 22, 24, a gantry rotation of approximately 90° ensures 180° of angular coverage for voxels contained in the central region 48. Assuming a 180° angular span of projections is sufficient to reconstruct the voxel, this gives an average temporal resolution for voxels contained in the central region 48 of about:

$$t_{res,central} = \frac{T_{gantry}}{4} = \frac{1}{4f_{gantry}}, \quad (1)$$

where $T_{gantry}$ is the period of gantry rotation, $f_{gantry}$ is the gantry rotation frequency, and $t_{res,central}$ is the temporal resolution for voxels in the central region 48. For an exemplary gantry rotation rate of $f_{gantry}$=200 rpm, $T_{gantry}$=300 milliseconds and $t_{res,central}$=75 milliseconds.

Outside of the central region 48, voxels are not irradiated continuously by the symmetric beam components. Moreover, some voxels contained in a surrounding region 50 that surrounds the central region 48 receive 180° angular coverage over a gantry rotational interval greater than 180° due to irradiation by the symmetric beam components and additional irradiation by the asymmetric beam components. This gives a temporal resolution for voxels contained in the surrounding region 50 that may be only about half the temporal resolution of the voxels in the central region 48. Hence, for the exemplary 200 rpm gantry rotation, there are voxels in the surrounding region that are completely reconstructed with a temporal resolution of only about 150 milliseconds.

In a preferred embodiment, the first radiation detector 30 has a high resolution detector portion 54 that receives the symmetric beam component of the first radiation 32, and a low resolution detector portion 56 that receives the asymmetric beam component of the first radiation 32. As seen in FIG. 2, the rays of the symmetric beam component of the first radiation 32 pass through the central region 48. Thus, the high resolution detector portion 54 receives that portion of the first radiation 32 that has passed through the central region 48. Also as seen in FIG. 2, the rays of the asymmetric beam component of the first radiation 32 pass through the surrounding region 50 but do not pass through the central region 48. Thus, the low resolution detector portion 56 receives that portion of the first radiation 32 that has passed through the surrounding region 50 but not through the central region 48. Similarly, the second radiation detector 34 has a high resolution detector portion 60 that receives the symmetric beam component of the second radiation 36 that has passed through the central region 48, and a low resolution detector portion 62 that receives the asymmetric beam component of the second radiation 36 that has passed through the surrounding region 50 but not the central region 48. It will be appreciated that if the collimators 26, 28 are reduced to their minimum settings so as to remove the asymmetric beam components, then the low resolution detector portions 56, 62 do not receive radiation.

In one embodiment, the detector portions 54, 56, 60, 62 all have detector elements of the same size. In this embodiment, detector elements of the high resolution detector portions 54, 60 have the same size as detector elements of the low resolution detector portions 56, 62. However, this embodiment of the radiation detectors 30, 34 is not optimal, because it is known that the image quality degrades for outlying portions of the imaging volume for various reasons, such as focus imperfections, increased x-ray scatter, reconstruction-related artifacts, and the like. Projection data acquired by the low resolution detector portions 56, 62 are generally less accurate compared with projection data acquired by the high resolution detector portions 54 60, due to the larger fan angle components of projections acquired by the low resolution detector portions 56, 62.

Therefore, in a preferred embodiment, detector elements of the low resolution detector portions 56, 62 have a larger size than detector elements of the high resolution detector portions 54, 60. This size difference can be obtained by fabricating different detector arrays with different array element sizes for the low resolution detector portions 56, 62 and for the high resolution detector portions 54, 60.

Alternatively, a single detector array or multiple arrays having the same array element size can be used for all detector portions 54, 56, 60, 62. In this embodiment, the larger detector elements of the low resolution detector portions 56, 62 are obtained by interconnecting a plurality of neighboring array elements to define each of the larger detector elements of the low resolution detector portions 56, 62. In a particularly preferred embodiment for a conebeam geometry, each low resolution detector element is constructed by interconnecting a square or rectangle of four array elements. In such an arrangement with exemplary array elements of 0.75 mm×0.75 mm array elements, the detector elements of the high resolution detectors 54, 60 each correspond to a single array element and thus have dimensions of 0.75 mm×0.75 mm, while the detector elements of the low resolution detector portions 56, 62 each correspond to four interconnected array elements and thus have dimensions of 1.5 mm×1.5 mm. In a fan-beam geometry that uses a linear detector array, neighboring pairs of array elements can be interconnected to reduce resolution from, for example, 0.75 mm, to 1.5 mm. In general, the interconnecting results in detector size for the low resolution detector portions 56, 62 being an integer multiple of detector size for the high resolution detector portions 54, 60.

In addition to embodying the high resolution detector portion 54, 60 and the low resolution detector portion 56, 62 as a single detector array by interconnecting array elements in the low resolution detector portion 56, 62, it is also similarly possible to combine the detector arrays 30, 34 as a single unitary detector array that is differentiated into the detector arrays 30, 34 functionally by the electrical connections. On the other hand, if different physical detector arrays are used for the first and second detector arrays 30, 34, then optionally the detector elements of the array 30 are differently sized from the detector elements of the array 34. However, to facilitate image reconstruction it is typically preferable to use detector elements of the same size for the high resolution detector portions 54, 60 of the two detector arrays 30, 34, and to similarly use detector elements of the same size for the low resolution detector portions 56, 62 of the two detector arrays 30, 34.

With continuing reference to FIG. 2, the first and second radiation detectors 30, 34 preferably further include corresponding first and second anti-scatter grids 66, 68 that are focused on the corresponding first and second radiation sources 22, 24. Each anti-scatter grid 66, 68 includes spaced-apart radiation-absorbing vanes aligned with radiation rays emanating from the corresponding radiation source 22, 24. In FIG. 2, only a few widely spaced representative vanes are shown. Existing anti-scatter grids include a higher density of more closely spaced vanes. The closely spaced vanes absorb scattered radiation while allowing direct radiation to pass between vanes substantially unattenuated. The radiation detectors 30, 34 are centered on the rotational center 38 rather than on the respective radiation sources 22, 24.

Figure 3:
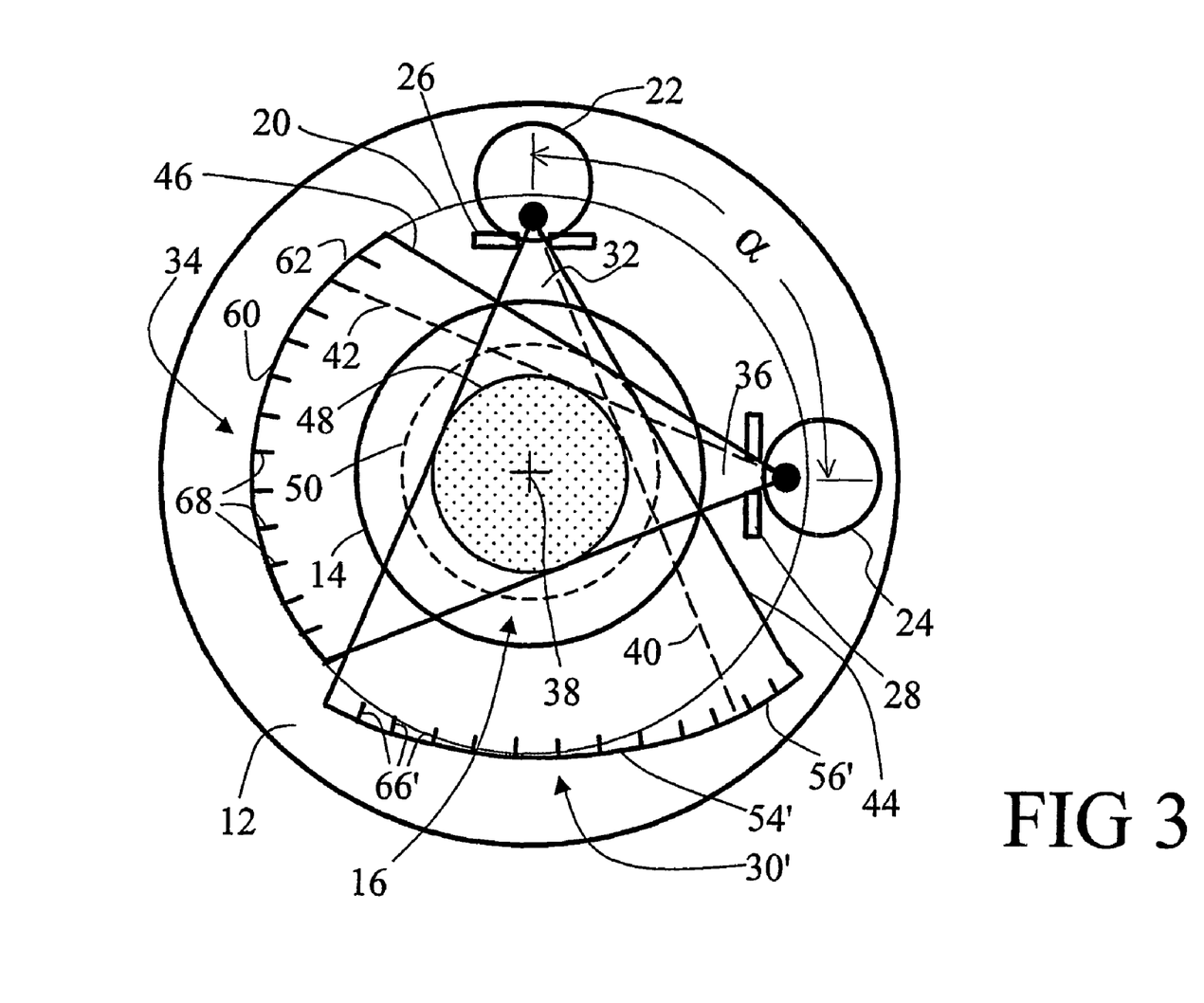
FIG. 3 diagrammatically shows another gantry embodiment of the computed tomography scanner of FIG. 1, in which one of the radiation detectors has detector elements at a constant radius from the source.

With reference to FIG. 3, in a modified embodiment, the rotationally centered first radiation detector 30 is replaced by a source-focused radiation detector 30' that includes high and low resolution portions 54', 56' analogous to the high and low resolution portions 54, 56 of the radiation detector 30. The source-focused radiation detector 30' has a curvature along the fan direction that is focused on the first radiation source 22. An anti-scatter grid 66' of the radiation detector 30' is also focused on the first radiation source 22. Optionally, the second radiation detector 34 can also be replaced by a source-focused radiation detector.

The source-focused radiation detector 30' advantageously enhances reconstruction speed by eliminating rebinning operations that compensate for the curvature mismatch between the radiation detector 30 and the position of the first radiation source 22. However, curvature mismatch between the source-focused radiation detector 30' and the rotating gantry 20 may complicate mechanical mounting and support of the source-focused radiation detector 30'. Moreover, if focal spot modulation is used, improved sampling obtained with the rotationally centered detector geometry provides improved spatial resolution over a substantial portion of the field of view.

With returning reference to FIGS. 1 and 2, those skilled in the art will recognize that there is a possibility of cross-talk between the first source-detector system 22, 30 and the second source-detector system 24, 34. First radiation 32 generated by the first radiation source 22 can scatter into the second radiation detector 34 and contribute to noise. Similarly, second radiation 36 generated by the second radiation source 24 can scatter into the first radiation detector 30 and contribute to noise. The anti-scatter grids 66, 68 substantially reduce such cross-talk noise by absorbing most of the scattered radiation. However, most radiation is scattered by small amounts with progressively less scatter at higher scattering angles. Detector elements in the vicinity of unattenuated scatter radiation will tend to receive the most cross-talk noise. Optionally, the height of the anti-scatter grid vanes in these areas are increased to reduce the cross-talk noise. As another option, a radiation source controller 70 causes the radiation output of the sources 22, 24 to alternate between radiation generation by the first radiation source 22 and radiation generation by the second radiation source 24 to ensure that only one of the radiation sources 22, 24 is generating radiation at any given time. In the case of x-ray vacuum tube sources, modulation of radiation generation from the sources 22, 24 is achieved in one contemplated embodiment by modulating an electrostatic potential of a grid in front of the tube filament to effect a substantial reduction or complete electrostatic pinchoff of the x-rays. By synchronizing sampling of the radiation detectors 30, 34 with the pulsed radiation generation of the radiation sources 22, 24 cross-talk can be substantially reduced.

In one preferred embodiment for interventional computed tomography applications, the scanner 10 has the following exemplary dimensions, in which all radii are referenced to the rotational center 38 of the rotating gantry 20. A radius $R_{bore}$ of the bore 14 is about 400 mm, providing a large 800 mm diameter opening for accommodating an imaging subject and instruments associated with the interventional procedure. The sources 22, 24 are arranged at a radius of 600 mm, while the radiation detectors 30, 34 are at a radius of 650 mm, so that the source-to-detector distance is about 1250 mm. The vanes of the anti-scatter grids 66, 68 extend about 50 mm radially inward. The fan angles and source-detector angular spacings are selected to define a radius $R_{central}$ of the high resolution central region 48 of about 200 mm, and a radius $R_{surround}$ of the low resolution surrounding region 50 of about 300 mm. In This preferred embodiment, the gantry rotates at about 200 rpm. These dimensions are exemplary only; those skilled in the art can readily select appropriate dimensions for specific applications.

With returning reference to FIG. 1, a support element 72, such as a couch, supports the imaging subject in the examination region 16, preferably with the region of interest substantially centered in the central region 48. Preferably, the support element 72 is linearly movable in an axial or z-direction (indicated in FIG. 1). The rotatable gantry 20 defines a gantry plane of gantry rotation. The axial or z-direction is generally transverse to the gantry plane of gantry rotation, and is preferably perpendicular thereto. In the fan-beam geometry, the support element 72 is optionally stepped between axial scans to acquire projection data for a plurality of axially spaced slices. In the conebeam geometry, stepped axial scans can also be used. Alternatively, in the conebeam geometry a continuous linear axial motion of the support element 72 is combined with simultaneous rotation of the gantry 20 during imaging to effect a helical orbit of the radiation sources 22, 24 about the imaging subject. For interventional computed tomography applications, the support element 72 typically remains stationary during the interventional procedure, and gantry rotation effects axial scanning that acquires images of a selected slice. Imaging data acquired by the first radiation detector 30 is stored in a first projection data memory 76, while imaging data acquired by the second radiation detector 34 is stored in a second projection data memory 78.

Figure 4:
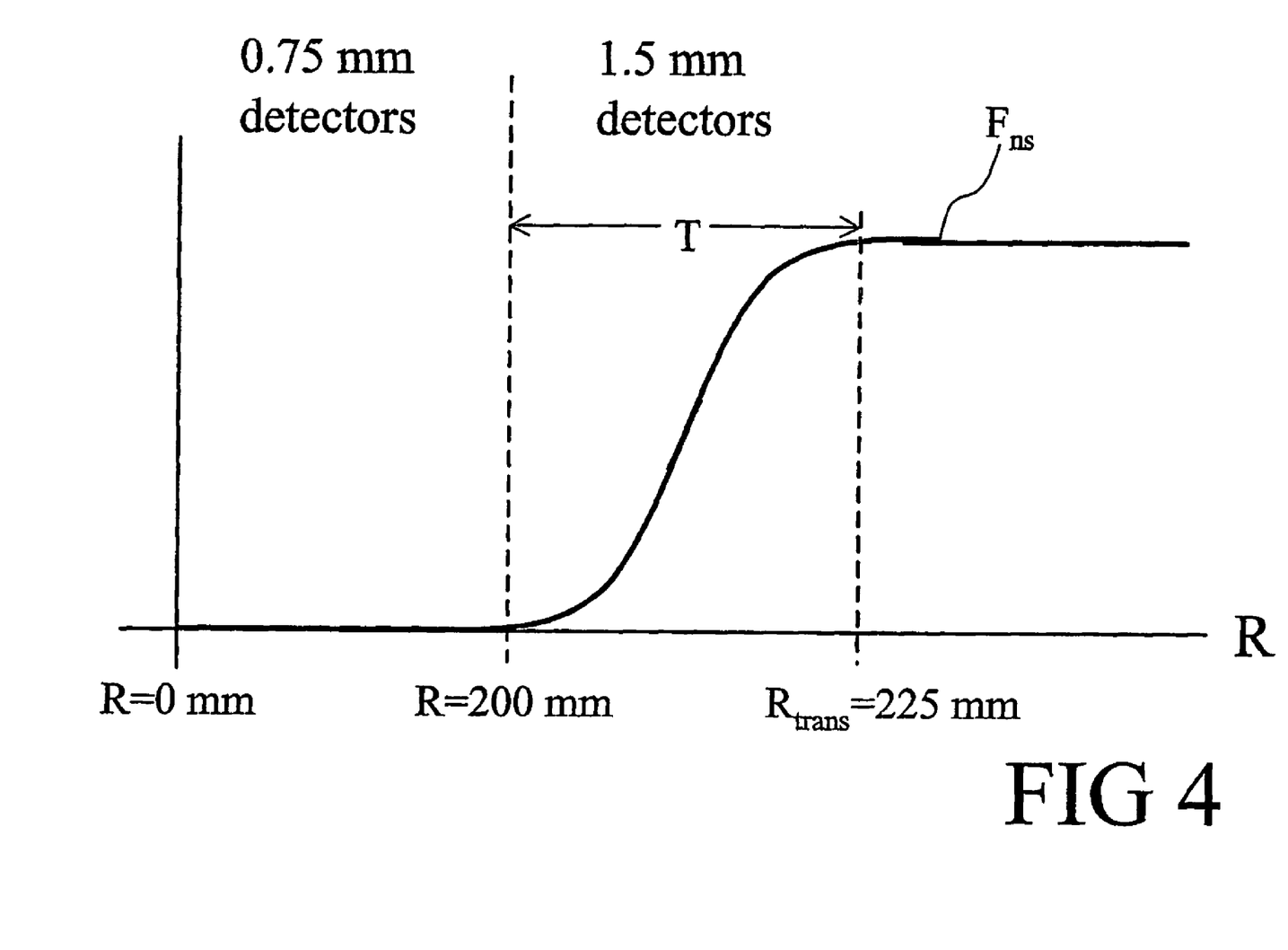
FIG. 4 shows a suitable non-stationary filter for smoothing a transition between projection data acquired using the high-resolution and low-resolution portions of the radiation detectors.

With continuing reference to FIG. 1 and with further reference to FIG. 4, non-stationary transition filters 80, 82 are applied to the projection data of stored in the first and second projection data memories 76, 78, respectively, to smooth a transition region T (indicated in FIG. 4) between the radius $R_{central}$ of the central region 48 and the surrounding region 50. In the exemplary dimensioned embodiment, the transition region T begins at about 200 mm and extends radially outward about 25 mm into the surrounding region 50. FIG. 4 diagrammatically shows a suitable non-stationary filter function $F_{ns}$, which is a function of radius R, for providing a smooth transition from the high resolution central region 48 to the low resolution surrounding region 50. Alternatively, the high and low resolution regions can be reconstructed separately and combined.

Figure 5:
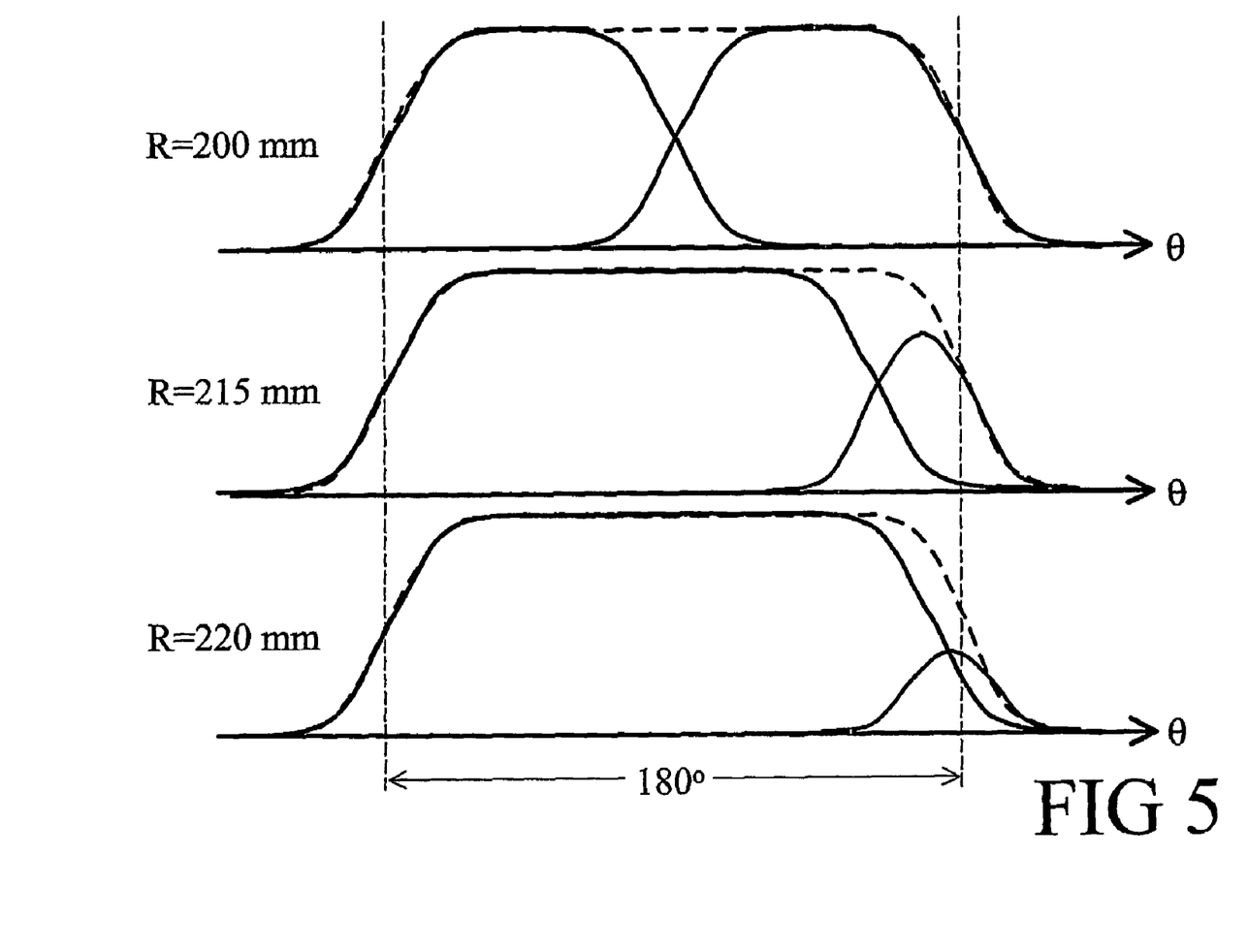
FIG. 5 shows exemplary angular weighting functions used in reconstructing voxels of the transition region.

With continuing reference to FIG. 1 and with further reference to FIG. 5, the smoothed data from the two detectors is input into a reconstruction processor 86 that reconstructs the smoothed projection data into one or more image representations. A voxel cycling processor 90 cycles through voxels of the field of view to be reconstructed. For each voxel, a weighting processor 92 weightedly combines projections that pass through the voxel and inputs the weighted projection data sets to a convolution backprojection processor 94. FIG. 5 shows exemplary weighting functions for voxels located at radii R=200 mm corresponding to an inner position of the transition region T, R=215 mm corresponding to an intermediate position within the transition region T, and R=220 mm corresponding to an outer position of the transition region T. These radii values are referenced to the exemplary dimensioned interventional computed tomography embodiment.

For voxels contained in the central region 48, that is, inside a radius of about 200 mm, a symmetric 90°+90° weighting is suitably applied that weights and combines angularly adjacent 90° segments acquired by the first and second radiation detectors 30, 34. The combined 90°+90° weighting covers 180° as indicated by the dashed line in FIG. 5. Outside the approximately 200 mm radius of complete coverage, weights vary depending upon voxel position. Generally, as the voxel radius increases through the transition region T, the weighting shifts toward a more asymmetric weighting with a reduction in temporal resolution reaching about a factor of two. Thus, at R=215 mm corresponding to an intermediate position within the transition region T, the weighting is relatively asymmetric, and by the radius R=220 mm corresponding to an outer position of the transition region T the weighting is substantially asymmetric. The weights shown in FIG. 5 for R=215 mm and R=220 mm are for select exemplary pixels at the indicated radii; in general the weights depend upon the angular position as well as the radius R. The weights further depend upon whether an axial or a helical reconstruction is performed. For each voxel, the net angular weighting (that is, the sum of the individual weights) provides 180° angular coverage, as indicated by the dashed line in the R=215 mm and R=220 mm weighting plots.

With reference to FIG. 1, the convolution backprojection processor 94 implements a suitable backprojection method such as a parallel-rebinned and filtered backprojection. The selected backprojection is preferably suitable for reconstructing a relatively large volume such as a field of view encompassing the central region 48 and the surrounding region 50. This field of view has a radius of about 300 mm in the exemplary dimensioned embodiment. Although the backprojection processor 94 implementing parallel-rebinned, filtered backprojection is illustrated, those skilled in the art can substitute other types of reconstruction processors that comport with specific computed tomography geometries, available processing hardware and software, and so forth.

The reconstructed image representation or image representations are stored in an image memory 98. The image representations are processed by a video processor 100 to produce an image slice, three-dimensional rendering, or other human-viewable representation, which is displayed on a display of a user interface 102. Rather than a video display, the contents of the image memory 98 can be printed, transmitted over a local computer network or the Internet, stored electronically, or otherwise processed. In a preferred embodiment, the user interface 102 also enables a radiologist or other system operator to interface with a computed tomography scan controller 104 to configure, initiate, and control the imaging process performed by the computed tomography scanner 10.

In the above-described reconstruction process, the first and second radiation sources 22, 24 produce first and second radiation 32, 36 that are generally monochromatic at the same energy. In this case the projection data acquired by the two radiation detectors 30, 34 is suitably weighted and combined to generate an image with improved spatial and temporal resolution due to the use of the two radiation sources 22, 24. In another contemplated embodiment, however, the radiation sources produce radiation at different energies. In this dual energy embodiment, projection data corresponding to each of the two radiation sources is separately reconstructed to produce images at the two different energies. Although, in this case, there is no improvement in temporal resolution, the two sets of images are acquired almost within a time interval of about $T_{gantry}/4$. This provides different tissue contrast for the two sets of images due to the difference in radiation energy. The images with separate tissue contrast can be displayed separately, or they can be superimposed, subtracted, or otherwise combined to target a selected tissue contrast. Alternatively, the projection data can be combined using a dual energy algorithm that optimally combines the projection data based on known spectra to target the selected tissue contrast, and the combined projection data set then reconstructed to produce a reconstructed image with the selected tissue contrast.

In one suitable embodiment, the first and second radiation sources 22, 24 are co-planar, that is, lie in a central plane of the gantry or in a plane parallel thereto. In this arrangement the first and second radiation sources 22, 24 acquire projection data for the same axial slice. In another contemplated embodiment, the first and second radiation sources 22, 24 are relatively axially offset by one-half of an axial spacing of detector elements of the radiation detectors 30, 34. This arrangement axially interleaves projections acquired by the first and second radiation detectors 30, 34 which reduces aliasing in the axial direction.

In yet another axially offset embodiment, the first source-detector pair 22, 30 and the second source-detector pair 24, 34 are separated axially by less than the axial dimension of the conebeam as measured at scan-center. This embodiment trades off improved temporal resolution for increased axial coverage for scans with circular orbits. Due to the angular separation of the radiation sources 22, 24, the two halves of the volume will be acquired with a temporal shift of approximately $T_{gantry}/4$. The two sets of acquired projections are preferably combined with a weighted transition region that corresponds to the amount of overlap between the two conebeams, and reconstructed to produce a volume with almost twice the coverage of a single circular orbit. The temporal resolution for voxels within the acquired volume will range from under $T_{gantry}/2$ to over $T_{gantry}$ (e.g., from less than 150 to over 300 milliseconds for the previous exemplary configuration).

In still yet another axially offset embodiment, conebeam helical computed tomography imaging (in which the support element 72 moves linearly simultaneously with rotation of the gantry 20) is performed with the first source-detector pair 22, 30 and the second source-detector pair 24, 34 relatively axially offset by an amount such that both sources 22, 24 rotate along a common helical orbit or along interleaved helical orbits. This arrangement provides improved temporal resolution by simultaneously acquiring helical data at two axially spaced positions. It is contemplated to mount one or both of the radiation source-detector pairs using an axially adjustable positioning mount that enables the relative axial spacing of the two source-detector pairs to be selectably adjusted. This enables, for example, the sources to be selectably spaced to correspond to a suitable fractional or whole helical pitch of the helical orbit.

Figure 6:
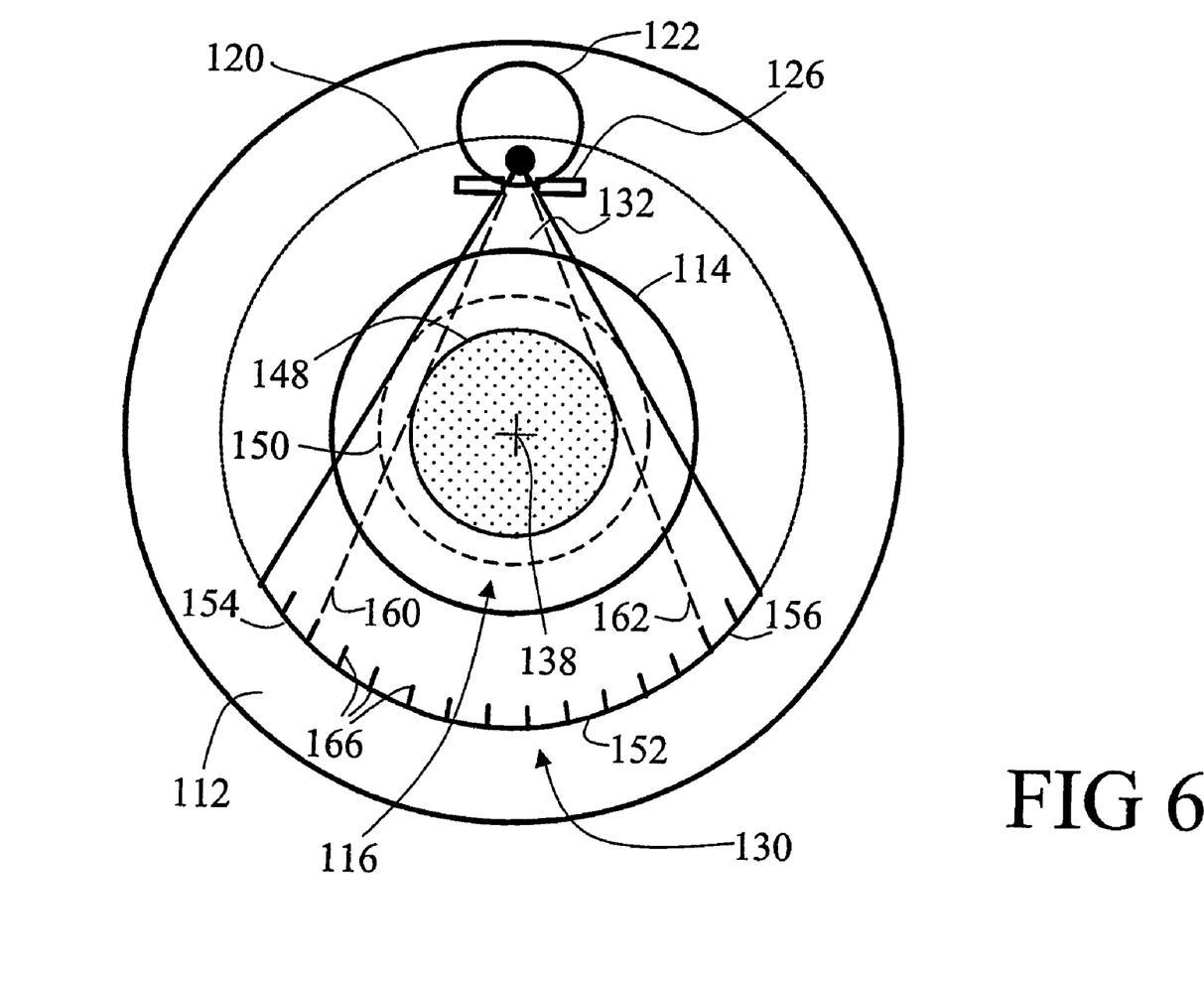
FIG. 6 diagrammatically shows a gantry supporting a single radiation source that operates in conjunction with a symmetric radiation detector including a high-resolution central detector portion and low-resolution outer detector portions.

With reference to FIG. 6, a single radiation source embodiment is described. A stationary gantry 112 has a bore 114 that defines an examination region 116. For interventional applications, the bore 114 is preferably a large bore, such as an 800 mm diameter bore. A rotating gantry 120 (indicated diagrammatically in FIG. 6) is rotatably mounted on the stationary gantry 114. A single radiation source 122 and associated collimator 126 that cooperatively produces a fan-beam or conebeam are arranged on the rotating gantry 120. The radiation source 122 is preferably an x-ray tube. A radiation detector 130 is arranged receive radiation 132 produced by the radiation source 122 after the radiation 132 passes through the examination region 116. The radiation detector 130 is arranged symmetrically with respect to the radiation source 122. That is, a center of the radiation detector 130 is angularly spaced from the radiation source 122 at 180° around the gantry.

A rotational center 138, that is, the center of gantry rotation, is indicated by crosshairs in FIG. 6. The radiation source 122 in cooperation with the collimator 126 produces the radiation 132 in an expanding fan-beam or conebeam configuration such that the radiation 132 expands at a fan-angle to substantially span the radiation detector 130. In the symmetric configuration of FIG. 6, the fan of the radiation 132 is symmetrically disposed about the rotational center 138. The fan angle is preferably large to provide imaging of a large field of view. Imaging in a central region 148 of the examination region 116 is of higher quality than imaging in a surrounding region 150. This is because imaging in the outlying surrounding region 150 is typically degraded due to focus imperfections, increased x-ray scatter, reconstruction-related artifacts, and the like.

The radiation detector 130 includes a high resolution central portion 152 interposed between two low resolution outer portions 154, 156. The outer portions 154, 156 are of equal area or angular span so that the radiation detector 130 is symmetric. An imaginary line or plane of demarcation 160 is defined that separates projection data acquired by the outer portion 154 and the central portion 152. Similarly, an imaginary line or plane of demarcation 162 is defined that separates projection data acquired by the outer portion 156 and the central portion 152. The low resolution outer portions 154, 156 have detector elements of a larger size than detector elements of the central portion 152 of the radiation detector 130. The detector 130 is suitably constructed similarly to the detectors 30, 34 of FIG. 2, for example by interconnecting array elements of the outer portions 154, 156 to form larger outer detector elements. Preferably, an anti-scatter grid 166 that includes radiation-absorbing vanes is disposed over the radiation detector 130 to reduce noise due to scattered radiation. Optionally, the anti-scatter grid 166 has different vane spacing or vane height, or both, in the central and outer detector portions 154, 156.

In one preferred embodiment for interventional computed tomography applications, the symmetric gantry of FIG. 6 has the following exemplary dimensions, in which all radii are referenced to the rotational center 138 of the rotating gantry 120. A radius of the bore 114 is about 400 mm, providing a large 800 mm diameter opening for accommodating an imaging subject and instruments associated with the interventional procedure. The radiation source 122 is arranged at a radius of 600 mm, while the radiation detector 130 is at a radius of 650 mm, so that the source-to-detector distance is about 1250 mm. The vanes of the anti-scatter grid 166 extend about 50 mm radially inward. The fan angle of the radiation 132 and the angular ratio of the outer low resolution detector portions 154, 156 to the central high resolution portion 152 of the radiation detector 130 are selected to define a radius of the high resolution central region 148 of about 200 mm, and a radius of the low resolution surrounding region 150 of about 300 mm. In this preferred embodiment, the gantry rotates at about 200 rpm. These dimensions are exemplary only; those skilled in the art can readily select appropriate dimensions for specific applications.

In the symmetric embodiment of FIG. 6, all voxels contained in either the central region 148 or the surrounding region 150 are continuously irradiated by the radiation source 122 during rotation of the gantry 120 for all gantry angles. Assuming a 180° angular span of projections is sufficient to reconstruct a voxel, this gives an average temporal resolution for voxels contained in either the central region 148 or the surrounding region 150 of about:

$$t_{res,symm} = \frac{T_{gantry}}{2} = \frac{1}{2f_{gantry}}, \quad (2)$$

where $T_{gantry}$ is the period of gantry rotation, $f_{gantry}$ is the gantry rotation frequency, and $t_{res,symm}$ is the temporal resolution for voxels. For an exemplary gantry rotation rate of $f_{gantry}$=200 rpm, $T_{gantry}$=300 milliseconds and $t_{res,central}$=150 milliseconds.

The spatial resolution is determined in part by the detector array resolution. In an exemplary embodiment, the central portion 152 of the radiation detector 130 has 0.75 mm elements, while in the outer portions 154, 156 neighboring detectors are interconnected to give a 1.5 mm resolution in the fan direction. The non-stationary transition filter $F_{ns}$ of FIG. 4 is suitably employed to smooth a transition region between the 0.75 mm resolution and 1.5 mm resolution regions. However, because only one radiation source 122 is used for imaging, the weighting windows of FIG. 5 are modified in that a 180°+180° weighting is applied to all voxels both in the central region 148 and in the surrounding region 150.

The use of radiation detector 130 with the high resolution central portion 152 and the outer low resolution portions 154, 156 beneficially increases reconstruction speed by reducing the amount of data for voxels in the surrounding region 150 which are of less interest for performing the interventional procedure. Optionally, the collimator 126 is symmetrically adjustable between the illustrated wide beam that is substantially coextensive with the radiation detector 130 and provides a large field of view, and a narrow beam (for example, restricted to the lines of demarcation 160, 162) that eliminates data at large fan angle to reduce radiation exposure at the expense of a narrower field of view.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A computed tomography imaging system including:
   a rotating gantry that rotates about an examination region along a longitudinal axis;
   a first radiation source disposed on the rotating gantry and arranged to emit first radiation into the examination region;
   a second radiation source disposed on the rotating gantry and arranged to emit second radiation into the examination region, the second radiation source being angularly spaced around the gantry from the first radiation source;
   a first asymmetrically adjustable collimator that is asymmetrically adjustable in a direction generally perpendicular to the longitudinal axis to position a first outer x-ray projection of the first radiation relative to a second outer x-ray projection of the first radiation;
   a second asymmetrically adjustable collimator that is asymmetrically adjustable in a direction generally perpendicular to the longitudinal axis to position a first outer x-ray projection of the second radiation relative to a second outer x-ray projection of the second radiation;
   a first radiation detector arranged to receive the first radiation, a center of the first radiation detector being angularly spaced around the gantry from the first radiation source by less than 180°;
   a second radiation detector arranged to receive the second radiation, a center of the second radiation detector being angularly spaced around the gantry from the second radiation source by less than 180°; and
   a reconstruction processor that reconstructs projection data acquired during gantry rotation by the first and second radiation detectors into one or more image representations;
   wherein the first asymmetrically adjustable collimator has a fixed collimation edge that defines the second outer x-ray projection of the first radiation and an adjustable collimation edge that defines the first outer x-ray projection of the first radiation,
   the second asymmetrically adjustable collimator has a fixed collimation edge that defines the second outer x-ray projection of the second radiation and an adjustable collimation edge that defines the first outer x-ray projection of the second radiation, and
   each of the adjustable collimation edges moves between a first position at which the first and second radiation is symmetrical about the rotational center and at least one other position at which the first and second radiation is asymmetrical about the rotational center.

2. The computed tomography imaging system as set forth in claim 1, wherein the first radiation detector includes:
   a high resolution portion having detector elements of a first size; and
   a low resolution portion having detector elements of a second size, the second size being larger than the first size.

3. The computed tomography imaging system as set forth in claim 2, wherein the second radiation detector includes:
   a high resolution portion having detector elements of the first size; and
   a low resolution portion having detector elements of the second size;
   wherein the high resolution portions of the first and second radiation detectors are arranged angularly between the low resolution portions of the first and second radiation detectors on the rotating gantry.

4. The computed tomography imaging system as set forth in claim 3, further including:
   a non-stationary filter that smooths a transition between projection data acquired by the low resolution portions of the first and second radiation detectors and projection data acquired by the high resolution portions of the first and second radiation detectors.

5. The computed tomography imaging system as set forth in claim 2, wherein:
   the angular spacing of the first radiation detector from the first radiation source by less than 180° defines symmetric and asymmetric beam components of the first radiation, the symmetric beam component being centered on a rotational center of the rotating gantry;

the high resolution portion of the first radiation detector is arranged to receive the symmetric beam component; and the low resolution portion of the first radiation detector is arranged to receive the asymmetric beam component.

6. The computed tomography imaging system as set forth in claim 1, wherein the first and second radiation detectors each span greater than 90° around the gantry.

7. The computed tomography imaging system as set forth in claim 1, wherein the second radiation source is angularly spaced from the first radiation source by 90°.

8. The computed tomography imaging system as set forth in claim 1, wherein the second radiation source is angularly spaced from the first radiation source by at least 90°, and each of the first and second radiation detectors spans greater than 90° around the gantry.

9. The computed tomography imaging system as set forth in claim 1, wherein the first and second radiation sources lie in a plane parallel to a plane of gantry rotation.

10. The computed tomography imaging system as set forth in claim 1, wherein the first and second radiation sources are relatively offset in an axial direction by one-half of an axial spacing of detector elements of the first and second radiation detectors.

11. The computed tomography imaging system as set forth in claim 1, wherein the first and second radiation sources are relatively offset in an axial direction by less than an axial dimension of a conebeam at a scan-center.

12. The computed tomography imaging system as set forth in claim 1, wherein the first and second radiation sources are conebeam radiation sources, and the first and second radiation detectors are two-dimensional arrays, the computed tomography imaging system further including:

a support element for supporting an associated imaging subject in the examination region, the support element being linearly movable in an axial direction, simultaneous gantry rotation and axial motion of the support element effecting a helical orbit of the first and second radiation sources relative to the associated imaging subject during acquisition of the projection data.

13. The computed tomography imaging system as set forth in claim 12, wherein the first and second radiation sources are relatively offset in the axial direction by an amount such that the second radiation source follows the first radiation source along the helical orbit.

14. The computed tomography imaging system as set forth in claim 1, wherein:

the first radiation detector includes a first anti-scatter grid focused on the first radiation source; and the second radiation detector includes a second anti-scatter grid focused on the second radiation source.

15. The computed tomography imaging system as set forth in claim 1, wherein:

a first radiation energy of the first radiation is different from a second radiation energy of the second radiation; and the reconstruction processor reconstructs projection data acquired by the first and second radiation detectors into one or more combined image representations having contributions from projection data acquired by the first and second radiation detectors.

16. The computed tomography imaging system as set forth in claim 1, further including:

a radiation source control that alternates between generating radiation by the first radiation source and generating radiation by the second radiation source such that the first and second radiation sources are not simultaneously generating radiation.

17. The computed tomography imaging system as set forth in claim 1, wherein the reconstruction processor includes:

a backprojector; and a weighting processor that applies a weighting function to projection data prior to backprojecting, the weighting processor applying a first weighting function to projection data for reconstruction of voxels in a central region of the examination region, the weighting processor applying a second weighting function for reconstruction of voxels outside the central region, the second weighting function being dependent upon a distance of the voxel outside the central region from the center of rotation.

18. A computed tomography imaging system including:

a rotating gantry defining an examination region, the examination region including a central region that contains a center of rotation of the rotating gantry and a surrounding region that surrounds the central region, the rotating gantry further defining a gantry plane of gantry rotation and an axial direction;

a first radiation source disposed on the rotating gantry, the first radiation source producing first radiation directed into the examination region;

a first radiation detector array arranged to receive the first radiation after the first radiation passes through the examination region, the first detector array including:

a high resolution portion with detector elements of a first size that receive first radiation that passes through the central region, and a low resolution portion with detector elements of a second size that receive first radiation that passes through the surrounding region but not the central region, wherein the second size is larger than the first size;

a second radiation source disposed on the rotating gantry, the second radiation source being positioned at an angular offset on the rotating gantry relative to the first radiation source, the second radiation source producing second radiation directed into the examination region;

a second radiation detector array arranged to receive the second radiation after the second radiation passes through the examination region, the second detector array including:

a high resolution portion with detector elements of a third size that receive second radiation that passes through the central region, and a low resolution portion with detector elements of a fourth size that receive second radiation that passes through the surrounding region but not the central region, wherein the fourth size is larger than the third size, wherein the high resolution portions of the first and second radiation detector arrays are arranged on the rotating gantry between the low resolution portions of the first and second radiation detector arrays;

wherein the first and second radiation detector arrays together define a single unitary radiation detector array, the single unitary radiation detector array including:

a central high resolution portion defined b the high resolution portions of the first and second radiation detector arrays;

a first outer low resolution portion defined by the low resolution portion of the first radiation detector array; and a second outer low resolution portion defined b the low resolution portion of the second radiation detector array, wherein the central high resolution portion is arranged between the first and second outer low resolution portions; and a reconstruction processor that reconstructs projection data acquired during gantry rotation by the first and second radiation detector arrays into an image representation.

19. The computed tomography imaging system as set forth in claim 18, further including:

a first asymmetrically adjustable collimator that is asymmetrically adjusted to move a first outer x-ray projection of the first radiation relative to a second outer x-ray projection of the first radiation; and a second asymmetrically adjustable collimator that is asymmetrically adjusted to move a first outer x-ray projection of the second radiation relative to a second outer x-ray projection of the second radiation.

20. The computed tomography imaging system as set forth in claim 19, wherein the first asymmetrically adjustable collimator has a fixed collimation edge that defines the second outer x-ray projection of the first radiation and an adjustable collimation edge that defines the first outer x-ray projection of the first radiation, and the second asymmetrically adjustable collimator has a fixed collimation edge that defines the second outer x-ray projection of the second radiation and an adjustable collimation edge that defines the first outer x-ray projection of the second radiation.

21. The computed tomography imaging system as set forth in claim 18, wherein the reconstruction processor includes:

a backprojector; and a weighting processor that weights the projection data prior to backprojecting, the weighting processor applying:

90° weighting windows for backprojecting voxels in the central region of the examination region, 180° weighting windows for backprojecting voxels in the surrounding region of the examination region, and asymmetric weighting windows for backprojecting voxels in a transition region intermediate between the central region and the surrounding region.

22. The computed tomography imaging system as set forth in claim 18, wherein the low resolution portion of each detector includes two low resolution sub-portions of equal size, the high resolution portion of each detector being disposed between the two low resolution sub-portions such that the first and second radiation detector arrays are symmetric detector arrays.

23. The computed tomography imaging system as set forth in claim 18, wherein each detector element of the low resolution portion of each detector includes a plurality of detector elements of the first size that are electrically interconnected.

24. A computed tomography imaging method including:

passing first radiation through an examination region, the examination region including a central region and a surrounding region;

measuring central projections, corresponding to rays of first radiation that intersect the central region, using a first high-resolution detector array that has a first spacing of detector elements;

measuring surrounding projections, corresponding to rays of first radiation that intersect the surrounding region without intersecting the central region, using a first low-resolution detector array that has a second spacing of detector elements, the second spacing being larger than the first spacing;

passing second radiation through the examination region;

measuring central projections, corresponding to rays of second radiation that intersect the central region, using a second high-resolution detector array that has the first spacing of detector elements;

measuring surrounding projections, corresponding to rays of second radiation that intersect the surrounding region without intersecting the central region, using a second low-resolution detector array that has the second spacing of detector elements; and reconstructing the central projections and the surrounding projections corresponding to the first radiation and the second radiation to generate a reconstructed image representation, wherein the reconstructing includes:

combining 90° contiguous angular segments of the central projections corresponding to the first radiation and the second radiation during reconstructing of voxels within the central region; and combining 180° contiguous angular segments of the central and surrounding projections corresponding to the first radiation and the second radiation during reconstructing of voxels in the surrounding region outside a transition radius.

25. The method as set forth in claim 24, wherein the first radiation is substantially monochromatic at a first energy and the second radiation is substantially monochromatic at a second energy that is different from the first energy, and the reconstructing includes:

reconstructing the central projections measured using the first high-resolution detector array and the surrounding projections measured using the first low-resolution detector array to generate a first reconstructed image representation; and reconstructing the central projections measured using the second high-resolution detector array and the surrounding projections measured using the second low-resolution detector array to generate a second reconstructed image representation.

26. The method as set forth in claim 24, wherein the passing of the first radiation and the passing of the second radiation do not overlap temporally.

* * * * *